United States Patent [19]
May et al.

[11] Patent Number: 5,681,834
[45] Date of Patent: Oct. 28, 1997

[54] HETEROCYCLIC SULFONAMIDES

[75] Inventors: Jesse A. May; Hwang-Hsing Chen; Anura Dantanarayana, all of Fort Worth; Abdelmoula Namil, Arlington, all of Tex.

[73] Assignee: Alcon Laboratories, Inc., Fort Worth, Tex.

[21] Appl. No.: 566,640

[22] Filed: Dec. 4, 1995

[51] Int. Cl.$^6$ .................... C07D 513/14; A61K 31/54
[52] U.S. Cl. ............................ 514/224.5; 544/33
[58] Field of Search ...................... 544/33; 514/224.5

[56] References Cited

U.S. PATENT DOCUMENTS 5,308,842 5/1994 Baldwin et al. ............. 514/224.5
5,378,703 1/1995 Dean et al. .................. 514/222.8

FOREIGN PATENT DOCUMENTS

WO 95/19981  7/1995  WIPO.

Primary Examiner—John M. Ford
Attorney, Agent, or Firm—Sally Yeager

[57] ABSTRACT

Compounds of the following structure are disclosed:

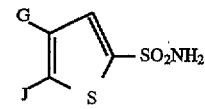

Wherein G, J and the two atoms of the thiophene ring to which they are attached are the group

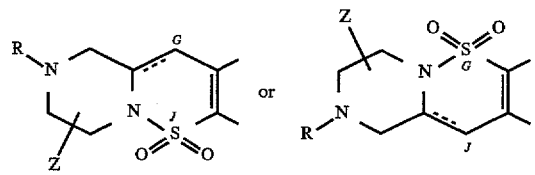

21 Claims, No Drawings

HETEROCYCLIC SULFONAMIDES

The present is directed to pyrazino [1,2-b]thieno[3,2-e]-1,2-thiazine-2-sulfonamides. The compounds are useful as carbonic anhydrase inhibitors.

BACKGROUND OF THE INVENTION

The disease state of glaucoma is characterized by a permanent loss of visual function due to irreversible damage to the optic nerve. The several morphologically or functionally distinct types of glaucoma are typically characterized by elevated intraocular pressure (IOP), which is considered to be causally related to the pathological course of the disease. Ocular hypertension is a condition wherein intraocular pressure is elevated but no apparent loss of visual function has occurred; such patients are considered to be a high risk for the eventual development of visual loss associated with glaucoma. If glaucoma or ocular hypertension is detected early and treated promptly with medications which effectively reduce elevated intraocular pressure, loss of visual function or its progressive deterioration can generally be ameliorated. Drug therapies which have proven to be effective for the reduction of intraocular pressure include both agents which decrease aqueous production and agents which increase the outflow facility. Such therapies are in general administered by one of two possible routes: topically (direct application to the eye) or orally.

Orally dosed carbonic anhydrase inhibitors (CAIs) have been used for approximately thirty years to assist in the maintenance of intraocular pressure. These agents inhibit the enzyme carbonic anhydrase, which is present in the ciliary process and intimately involved in the production of aqueous humor. CAIs act through their ability to decrease the production of aqueous humor. Though CAIs are efficacious and nontoxic to ocular tissues following oral administration, they do muse an array of detrimental, systemic (extraocular) side effects. The most serious, but rare, side effects are life-threatening blood dyscrasia and the formation of renal calculi. The more common side effects are nausea, dyspepsia, fatigue, impotence, depression, metabolic acidosis, and others which, although not generally life threatening, are sufficiently debilitating that patients frequently choose to discontinue therapy, particularly older patients who are less able to tolerate these side effects.

There is, therefore, a clear need for CAIs which are topically effective, thereby eliminating or significantly reducing the detrimental side effects associated with oral administration. The compounds of the present invention are new sulfonamides which are carbonic anhydrase inhibitors useful for lowering IOP without producing significant systemic side effects when delivered topically to the eye.

SUMMARY OF THE INVENTION

The present invention is directed to CAIs which are useful in lowering and controlling IOP associated with ocular hypertension and glaucoma in warm blooded animals, including man. The compounds are formulated in pharmaceutical compositions suitable for topical delivery to the eye.

The invention is also directed to methods for lowering and controlling IOP by the administration of the compositions comprising the sulfonamides of the present invention topically to the eye.

DETAILED DESCRIPTION OF THE INVENTION

The CAIs of the present invention have the following structure:

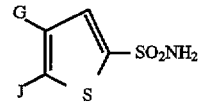

I

Wherein G, J and the two atoms of the thiophene ring to which they are attached are the group

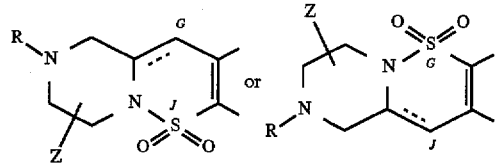

wherein

Z is hydrogen, $C_{1-4}$alkyl, $C_{1-4}$alkyl substituted with one or more of hydroxyl, $C_{1-4}$alkoxy, $C_{2-4}$alkoxy-$C_{1-4}$alkoxy, $OC(=O)R^1$, $N(R^2)C(=O)R^1$, halogen, $NR^2R^3$ or $C(=O)R^4$; $C_{1-4}$alkyl substituted with an aromatic group chosen from phenyl or Q, either of which is unsubstituted or substituted with one or more of $C_{1-4}$alkyl, $C_{1-4}$ alkoxy, hydroxy, halogen, $NR^2R^3$, $C(=O)R^4$ or $C_{1-4}$alkyl which is substituted with hydroxy, $NR^2R^3$, halogen, $CO^2R^1$, or $C_{1-3}$alkoxy;

R is hydrogen, $C_{1-4}$alkyl, $C_{1-4}$alkoxy, $C(=O)R^1$, $C_{1-4}$alkyl substituted by $C_{1-4}$alkoxy, $CO_2$-$C_{1-4}$ alkyl, halo, $NR^2R^3$, $OC(=O)$-$C_{1-4}$alkyl, hydroxyl, or $C(=O)NR^2R^3$;

$R^1$ is $C_{1-4}$alkyl; $C_{1-6}$alkyl substituted with hydroxyl, halogen, $C_{1-4}$alkoxy, or $NR^2R^3$;

$R^2$ and $R^3$ are independently hydrogen;
$C_{1-4}$alkyl;
$C_{1-3}$alkyl-$C_{3-6}$cycloalkyl;
$C_{2-4}$alkyl substituted with hydroxyl, halogen, CN, $C_{1-4}$alkoxy, or $C(=O)R^4$;
hydroxyl;
$C_{1-4}$alkoxy;
$C_{2-4}$alkoxy substituted with hydroxyl, $NR^2R^3$, halogen, or $C_{1-4}$alkoxy;
$C_{3-8}$alkenyl unsubstituted or substituted with hydroxy, or $C_{1-4}$alkoxy; or further $R^2$ and $R^3$ together with the nitrogen atom to which they are attached are incorporated into a saturated heterocyclic ring chosen from pyrrolidine, oxazolidine, morpholine, thiomorpholine, thiomorpholine 1,1-dioxide, 2-oxa-5-azabicyclo[2.2.1]heptane, 2-oxa-5-azabicyclo[3.2.1]octane, thiazolidine, or thiazolidine 1,1-dioxide, which are unsubstituted or substituted on carbon with hydroxyl, (=O), halogen, $C_{1-4}$alkoxy, $C(=O)R^4$, $C_{1-4}$alkyl, $C_{1-4}$aklcyl substituted with hydroxyl, halogen, $C_{1-4}$alkoxy, or $C(=O)R_4$;

$R^4$ is hydroxyl; $C_{1-4}$alkoxy;
$C_{2-4}$alkoxy substituted with hydroxyl, $NR^2R^3$, halogen or $C_{1-4}$alkoxy; $NR^2R^3$;

Q is a heterocycle selected from the group consisting of thiophene, furan, pyrrole, pyrazole, imidazole, triazole, tetrazole, oxazole, isoxazole, isothiazole, thiazole, thiadiazole, pyridine, pyrimidine, pyridazine, and pyrazine.

The dashed bond indicates that this particular bond can be either a double bond or a single bond.

In compounds of structure I which are pyrazino[1,2-b]thieno[3,2-e]-1,2-thiazines, substituent Z can be attached at positions 5, 7, or 8; and, in compounds of structure I which are pyraino[1,2-b]thieno[2,3-e]-1,2-thiazines, substituent Z can be attached at positions 6, 7, or 9. Independent variations of substituent Z can be attached at more than one of these positions. In the preferred embodiments of this invention substituent Z, when other than hydrogen, is attached at position 7. Selected compounds of Structure I can possess one or more chiral centers, this invention contemplates all enantiomers, diastereomers, and mixtures thereof.

In the above definitions, the total number of carbon atoms in a substituent group is indicated in the form $C_{i-j}$ where the numbers i and j define the number of carbon atoms; this definition includes straight chain, branched chain, and cyclic alkyl groups.

It is important to recognize that a substituent may be present either singly or multiply when incorporated into the indicated structural unit. For example, the substituent halogen, which means fluorine, chlorine, bromine, or fluorine, would indicate that the alkyl or aryl portion to which it is attached may be substituted with one or more halogen atoms, which may be the same or different.

Synthesis

Certain desirable compounds of Formula I can be prepared from 3-thiophenecarboxaldehyde acetals (1) according to Equation 1. The incorporation of a substituted sulfonamide at position two of the thiophene acetal (1) can be accomplished by treatment with a strong organometallic base such as n-butyllithium to form the organolithium intermediate which can be reacted with an appropriate electrophile to provide the desired sulfonyl chloride, such as sulfuryl chloride, or sulfur dioxide followed by reaction of the intermediate lithium site with N-chlorosuccinimide. Subsequent reaction of the sulfonyl chloride with glycine ethyl ester provides the thiophene-2-sulfonamide 2. Cleavage of the acetal to the aldehyde can be readily accomplished under acidic conditions; subsequent alkylation with the desired substituted alkyl halide (designated W-X in Equation 1) under basic conditions, e.g. potassium carbonate or NaH, with concomitant cyclization provides the thieno[3,2-e]-1, 2-thiazine intermediate 3 (see also WO 95/19981). Reduction of the ester group by any of a variety of conditions known to the art, for example diisobutylaluminium hydride, provides intermediate 4 bearing a hydroxymethyl group at position three. The requisite primary sulfonamide functionality can be introduced at this point by treatment of 4 with n-butyllithium and sulfur dioxide, as for the preparation of 2, but instead, reacting the intermediate lithium sulfinate with an electrophilic mating reagent, for example, hydroxylamine-O-sulfonic acid, to provide the intermediate sulfonamide diol 5. Activation of the hydroxyl groups toward subsequent nucleophilic amination can be accomplished by formation of a sulfonate ester, e.g. toluenesulfonyl, methanesulfonyl; treatment of the disulfonate ester with the desired primary amine or ammonia provides compounds of Formula I.

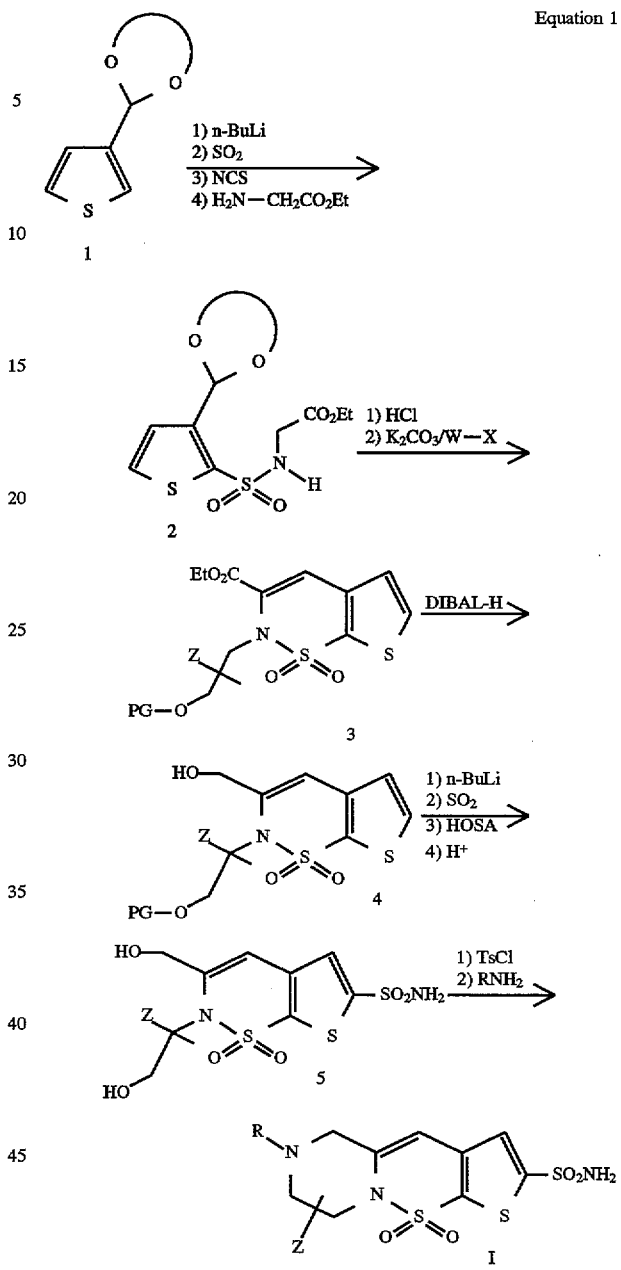

Equation 1

Alternately, compounds of Formula I specifically substituted at position seven can be prepared according to Equation 2. For example, alkylation of the aldehyde obtained from 2 with an appropriately activated, i.e. halide or sulfonate ester, and protected alkyldiol (designated W-X in Equation 2) with concomitant cyclization provides the thieno[3,2-e]-1,2-thiazine intermediate 6. Subsequent treatment under acidic conditions, e.g. trifluoroacetic acid, provides deprotection of the diol with concomitant cyclization to a hydroxymethyl lactone; protection of the hydoxyl group provides intermediate lactone 7. Lactone 7 can be readily reduced to the dihydroxy intermediate 8 under any of a variety of condition well known to the art, e.g. diisobutylaluminium hydride. Conversion of the dihydroxy intermediate 8 to desired compounds of Formula I can be accomplished as described in Equation 1. The 7-hydroxyalkyl substituted compounds prepared according to Equation 2 can be further modified by any of a variety of functional group transformations well known in the art, for example, conversion to esters, amines, or amides, among others.

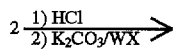

Equation 2

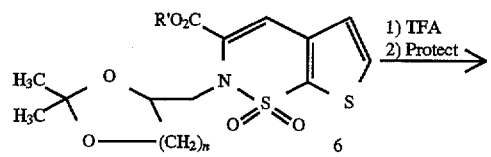

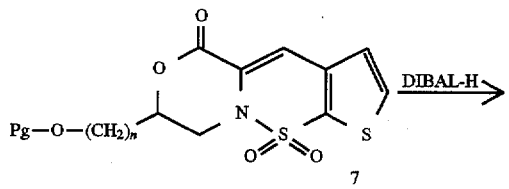

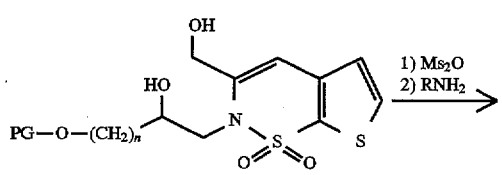

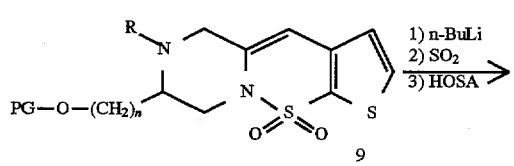

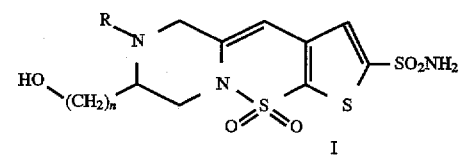

Additional compounds of Formula I wherein substituent Z is at position five can be prepared according to Equation 3. Saponification of ester 3 provides acid 10 which when converted to the lithium salt followed by treatment with an organolithium compound (designated Z-Li in Equation 3) provides the ketone 11. Reduction of the ketone by any of a variety of procedures known to the art, such as sodium borohydride, followed by removal of the protection group under acidic condition provides the diol 12. Transformation of 12 to compounds of Formula I can be accomplished as described in Equations 1 and 2.

Equation 3

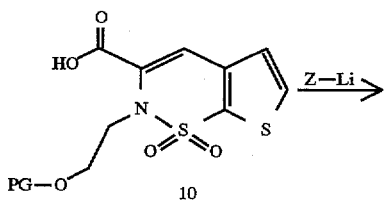

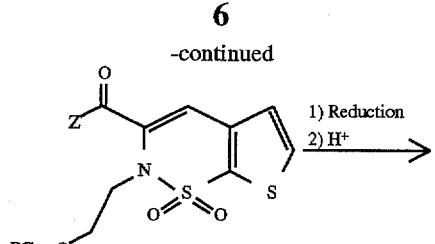

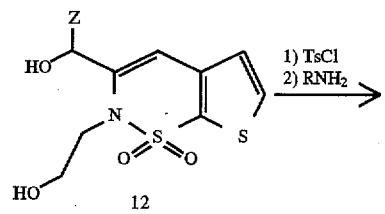

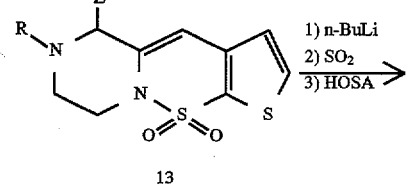

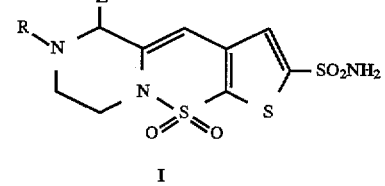

Other compounds of Formula I, such as 4,4a,5,6,7,8-hexahydro-pyrazino[1,2-b]thieno[3,2-e]-1,2-thiazine-2-sulfonamide 10, 10-oxides, can be prepared according to Equation 4. Reaction of compound 3 with a reducing agent suitable for the reduction of both the ester group and the olefin bond, for example sodium borohydride, provides intermediate 14. Introduction of the required sulfamoyl group can be accomplished by reacting 14 under conditions similar to those described in Equation 1 to provide 15. Cleavage of protecting groups provides the diol which, following activation as an appropriate sulfonate ester and reaction with the desired amine (Equation 1), provides yet additional novel compounds of Formula I.

Equation 4

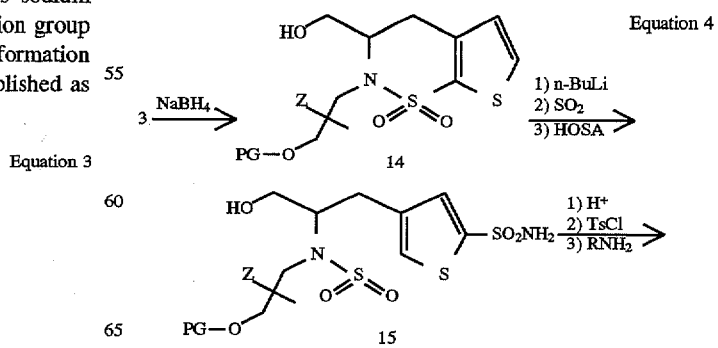

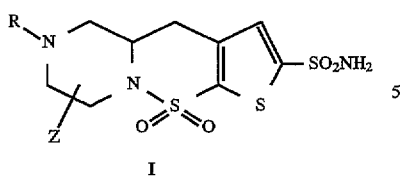

I

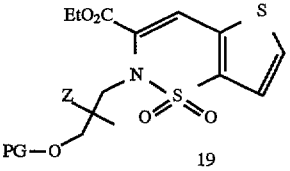

19

Yet other desirable compounds of Formula I, namely substituted 5,6,7,8-tetrahydro-pyrazino[1,2-b]thieno[2,3-e]-1,2-thiazine-2-sulfonamide 10,10-dioxides, can be prepared in a manner analogous to that already described for substituted 5,6,7,8-tetrahydro-pyrazino [1,2-b]thieno[3,2-e]-1,2-thiazine-2-sulfonamide 10, 10-dioxides in Equation 2, but using instead acetal 16 as starting material (Equation 5). Selective metallation of 2,3-dibromothiophene with an organolithium base and subsequent treatment with an N, N-dialkylformamide, such as N, N-dimethylformamide or N-formylpiperidine, provides 3-bromo-2-thiophenecarboxaldehyde which can be protected as the acetal 16. Introduction of the desired substituted sulfonamide at position three of acetal 16 to give intermediate 17 can be accomplished in a manner analogous to that already described for thiophene acetals in Equation 1. It can be advantageous in certain cases to react the intermediate sulfonyl chloride prepared from 16 directly with an N-substituted glycine ester to provide intermediate 18. Cyclization of intermediate 18 in the presence of an organic base following the deprotection of the acetal provides intermediate 19. Subsequent transformation of 19 to compounds of Formula I proceeds as described in Equation 1.

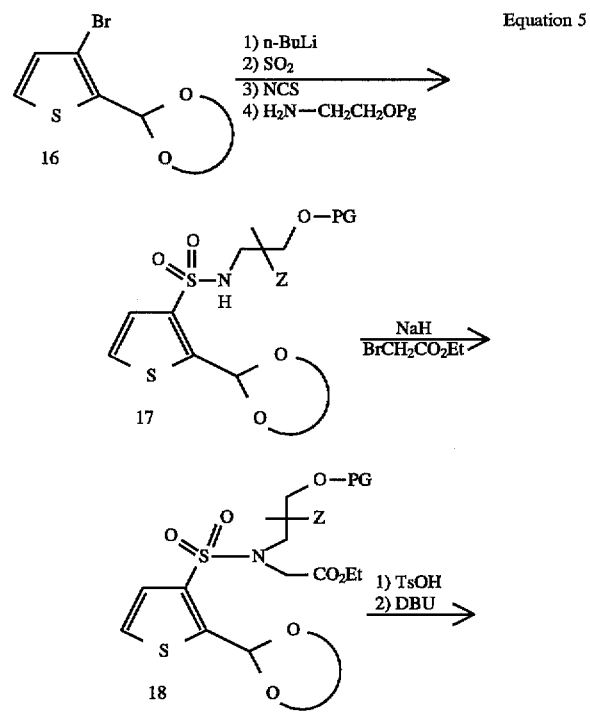

Equation 5

The compounds of this invention, Formula I, can be incorporated into various types of ophthalmic formulations for delivery to the eye. For example, these compounds can be combined with ophthalmologically acceptable preservatives, surfactants, viscosity enhancers, penetration enhancers, buffers, sodium chloride, and water to form an aqueous, sterile ophthalmic suspension or solution.

In order to prepare sterile ophthalmic ointment formulations, the active ingredient is combined with a preservative in an appropriate vehicle, such as, mineral oil, liquid lanolin, or white petrolatum. Sterile ophthalmic gel formulations may be prepared by suspending the active ingredient in a hydrophilic base prepared from the combination of, for example, Carbopol-940 or the like (carboxy vinyl polymers available from B. F. Goodrich Company) according to published formulation for analogous ophthalmic preparations; preservatives and tonicity agents can be incorporated.

Ophthalmic solution formulations may be prepared by dissolving the active ingredient in a physiologically acceptable isotonic aqueous buffer. The ophthalmic solution may include an ophthalmologically acceptable surfactant to assist in dissolving the active ingredient and a thickener, such as, hydroxymethylcellulose, hydroxypropylcellulose, methylcellulose, polyvinylpyrrolidone, or the like to improve the retention of the medicament in the conjunctival sac.

Ophthalmic solution, suspensions, ointments, gels, are the preferred dosage forms, typically at pH 4–8, the physiologically acceptable range for ophthalmic administration. The compounds will normally be contained in these formulations in the amount of 0.1% to 10% by weight (wt. %), but preferably in an amount of 0.25 to 5 wt.%. Thus, for topical presentation these formulations would be delivered to the surface of the eye 1–4 times/day depending upon the discretion of a skilled clinician.

The following examples are given to illustrate the preparation of compounds which are the subject of this invention but should not be construed as implying any limitations to the claims. The preferred compounds of Formula 1 are 6-substituted, 7-substituted, and 6,7-disubstituted 5,6,7,8-tetrahydro-pyrazino[1,2-b]thieno[3,2-e]-1,2-thiazine-2-sulfonamide 10,10-dioxides. Most preferred are 6-substituted and 7-substituted 5,6,7,8-tetrahydro-pyrazino [1,2-b]thieno[3,2-e]-1,2-thiazine-2-sulfonamide 10,10-dioxides. Especially preferred compounds are those set forth in Examples 1, 2, and 5. The proton magnetic resonance spectrum of each compound of the Examples was consistent with the assigned structure.

EXAMPLE 1

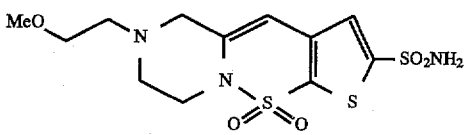

5,6,7,8-Tetrahydro-6-(2-methoxyethyl)-pyrazino[1,2-b]thieno[3,2-e]-1,2-thiazine-2-sulfonamide 10,10-dioxide Step A: 3-(2-Dioxolanyl)-N-(2-hydroxyethyl)thiophene-2-sulfonamide To a solution of thiophene-3-carboxaldehyde ethylene acetal (25.0 g, 160 mmol) in anhydrous THF (300 mL) under nitrogen at −70° C. was added n-butyllithium (2.5M, 76.9 mL, 192 mmol) over a 10 min period. The mixture was stirred for 40 min during which a white precipitate formed. Sulfur dioxide was passed over the mixture for about 10 min and the mixture was warmed to ambient temperature. The volatiles were evaporated and the residue was mixed with methylene chloride (400 mL), cooled to 0° C and N-chlorosuccinimide (29.9 g, 224 mmol) was added. The mixture was stirred for 2 h at ambient temperature and filtered through a bed of filter aid which was washed with ethyl acetate (400 mL). The filtrate was cooled on an ice bath and ethanolamine (30 mL) was added. The reaction mixture was stirred for 1 h and a saturated solution of sodium bicarbonate (200 mL) added. The organic layer was separated, dried over magnesium sulfate, filtered and evaporated to dryness. Column chromatography (silica, gradient, 60% ethyl acetate in hexane) gave the desired product as an oil (35.72 g, 80%).

Step B: N-[2-(1-Ethoxyethoxy)ethyl]-N-[(3-formyl-2-thienyl)sulfonyl]glycine ethyl ester To a stirred solution of the product from Step A (11.55 g, 41.4 mmol) in anhydrous DMF (200 mL) at 0° C. was added NaH (60% dispersion in mineral oil, 1.74 g, 43.5 mmol). After 30 min ethyl bromoacetate (5.51 mL, 6.33 g, 49.7 mmol) was added; this solution was stirred for about 7 min and 2N HCl (100 mL) added. The resulting mixture was stirred at ambient temperature for 2 h, poured into ice-water (300 mL) and extracted with ethyl acetate (2×300 mL). The combined extracts were dried over magnesium sulfate, filtered and evaporated to dryness to give a viscous oil which was dissolved in THF (50 mL), p-TsOH (0.1 g) was added and the solution cooled on an ice bath followed by the addition of ethyl vinyl ether (7.86 mL, 82.2 mmol). After stirring for 1 h a saturated solution of sodium bicarbonate (100 mL) was added and the mixture was extracted with ethyl acetate (2×200 mL). The combined extracts were dried over magnesium sulfate, filtered and evaporated to dryness. Column chromatography (silica, 30% ethyl acetate in hexane) gave the desired product as a viscous oil (10.21 g, 63%).

Step C: Ethyl 2-[2-(1-ethoxyethoxy)ethyl]-2H-thieno[3,2-e]-1,2-thiazine-3-carboxylate 1,1-dioxide To a mixture of the product from Step B (10.2 g, 25.9 mmol) and molecular sieves (10 g) in ethyl acetate (150 mL) was added DBU (1 mL). The mixture was stirred overnight at ambient temperature, poured into a sainted solution of sodium bicarbonate (150 mL), and the organic layer was separated, dried and evaporated to give an oil (8.89 g, 91%).

Step D: 2-(2-Hydroxyethyl)-3-hydroxymethyl-2H-thieno[3,2-e]-1,2-thiazine 1,1-dioxide To a solution of the product from Step C (8.77 g, 23.4 mmol) in anhydrous ether (100 mL) at 0° C. was added diisobutylaluminium hydride (1M solution in hexanes, 70.2 mmol). The reaction mixture was stirred for 1 h, a solution of potassium sodium tartrate (28.2 g in 100 mL water) was added, and the resulting mixture stirred for 2 h. The aqueous layer was separated and extracted with ethyl acetate (2×100 mL). The combined extracts were dried over magnesium sulfate, filtered and evaporated to give an oil which was dissolved in acetone (100 mL) and treated with 100 mL of 2 N HCl for 4 h. The acetone was evaporated and the remaining aqueous mixture was extracted with ethyl acetate (2×100 mL) The combined extracts was dried and evaporated to give a solid (4.82 g, 79%); Recrystallization from EtOAc/Hex gave a crystalline solid: mp 81°–83° C.

Step E: 5,6,7,8-Tetrahydro-6-(2-methoxyethyl)-pyrazino[1,2-b]thieno[3,2-e]-1,2-thiazine 10,10-dioxide Hydrochloride To a solution of the product from Step D (1.37 g, 5.25 mmol and trimethylamine (2.12 g, 21.0 mmol) in methylene chloride (100 mL) at 0° C. was added p-toluenesulfonyl chloride (2.50 g, 13.13 mmol). The mixture was stirred for 3 h, cooled (about 7° C.) overnight, and 2-methoxyethylamine (5 mL) was added, followed by stirring for 2 h at ambient temperature and heating at reflux temperature for 2 h. A saturated solution of sodium bicarbonate (80 mL) was added to the reaction mixture which was extracted with ethyl acetate (2×80 mL). The combined extracts were evaporated to a residue which was purified by column chromatography (silica, ethyl acetate) to give a viscous oil (0.98 g, 62%). Dissolution of the oil in ethyl acetate (50 mL) and treatment with 2N HCl/EtOH (2 mL) provided a crystalline solid which was collected by filtration and dried to give a colorless solid: mp 208°–210° C.

Step F: 5,6,7,8-Tetrahydro-6-(2-methoxyethyl)-pyrazino[1,2-b]thieno[3,2-e]-1,2-thiazine-2-sulfonamide 10,10-dioxide To a solution of the product from Step E (1.96 g, 6.53 mmol) in anhydrous THF (40 mL) under nitrogen at −70° C. was added n-butyllithium (2.5M in hexanes, 2.87 mL, 7.19 mmol). The mixture was stirred for 10 min and a stream of sulfur dioxide passed over the surface of the reaction mixture for about 3 min. The mixture was warmed to ambient temperature, evaporated to dryness, and the residue was mixed with water (80 mL), cooled on an ice bath and hydroxylamine-O-sulfonic acid (1.84 g, 16.3 mmol) and sodium acetate (3.55 g, 26.1 mmol) were added. The reaction mixture was stirred at ambient temperature for 4 h, mixed with a saturated solution of sodium bicarbonate (100 mL) and extracted with ethyl acetate (2×200 mL). The combined extracts were dried over magnesium sulfate, filtered and evaporated to give a solid (1.39 g) which was dissolved in ethyl acetate, filtered through a short silica column with ethyl acetate and evaporated to dryness. Recrystallization from acetonitrile gave a solid (0.69 g, 28%): mp 180°–182° C.

Analysis. Calculated for $C_{12}H_{17}N_3O_5S_3$: C, 37.98; H, 4.52; N, 11.07. Found: C, 38.08; H, 4.54: N, 11.04.

EXAMPLE 2

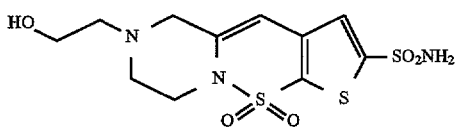

5,6,7,8-Tetrahydro-6-(2-hydromethyl)-pyrazino[1,2-b]thieno[3,2-e]-1,2-thiazine-2-sulfonamide 10,10-dioxide To a stirred suspension of the product from Example 1 (0.353 g, 0.931 mmol) in methylene chloride (50 mL) at 0° C. was added bromodimethylborane (0.364 mL, 3.72 mmol). The mixture was warmed to ambient temperature and stirred overnight. A 2M solution of borontribromide in methylene chloride (2 mL) was added and the mixture was stirred overnight. The mixture was evaporated to dryness, mixed with a saturated solution of sodium bicarbonate (50 mL) and extracted with ethyl acetate (2×60 mL). The combined extracts were dried over magnesium sulfate and evaporated to an oil which was purified by column chromatography (silica, gradient 5% to 10% methanol in methylene chloride) to give a solid (0.236 g, 69%): mp 192°–194° C.

Analysis. Calculated for $C_{11}H_{15}N_3O_5S_3$: C, 36.15; H, 4.14; N, 11.50. Found: C, 36.25; H, 4.16; N, 11.43.

EXAMPLE 3

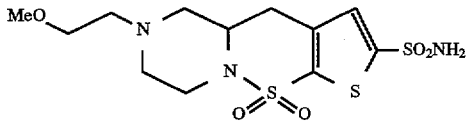

4,4a,5,6,7,8-Hexahydro-6-(2-methoxyethyl)-pyrazino[1,2-b]thieno[3,2-e]-1,2-thiazine-2-sulfonamide 10,10-dioxide Step A: N-[[3-(1,3-dioxolan-2-yl)-2-thienyl]sulfonyl]glycine ethyl ester To a solution of thiophene-3-carboxaldehyde ethylene acetal (13.27 g, 85.1 mmol) in anhydrous THF (200 mL) at −70° C. was added n-butyllithium (2.5M, 37.4 mL, 93.6 mmol). The solution was stirred for 50 min; a white precipitate formed. Sulfur dioxide was passed through the solution for about 5 min and the mixture was warmed to ambient temperature. The volatiles were evaporated and the residue suspended in methylene chloride (200 mL); this mixture was cooled (0° C.) and N-chlorosuccinimide (14.77 g, 110.6 mmol) added. After stirring at ambient temperature for 3 h the mixture was filtered. The filter pad was washed with ethyl acetate (300 mL) and the combined filtrates were cooled (ice bath) and mixed with a saturated aqueous solution of sodium bicarbonate (250 mL) and glycine ethyl ester hydrochloride (33.99 g, 221 mmol). The mixture was stirred at ambient temperature for 16 h and the organic layer was separated, dried (MgSO$_4$), and evaporated to a residue which was purified by column chromatography (silica, 40% ethyl acetate in hexane) to give a colorless liquid (16.55 g, 61%).

Step B: N-[(3-formyl-2-thienyl)sulfonyl]glycine ethyl ester

To a solution of the product from Step A (31.0 g 97.0 mmol) in THF (100 mL) was added 3N HCl and the mixture stirred for 6 h at room temperature. Brine (100 mL) was added and the mixture extracted with ethyl acetate (3×100 mL). The combined extracts were washed with brine (20.0 mL), dried (MgSO$_4$) and evaporated to yield a white solid (22.0 g, 82%): mp 74°–76° C.

Step C: Ethyl 2-[2-(methoxymethoxy)ethyl]-2H-thiophene[3,2-e]-1,2-thiazine-3-carboxylate 1,1-dioxide To a stirred solution of the product from Step B (31.0 g, 111.9 mmol) in DMSO (80 mL) was added potassium carbonate (46.4 g, 336.0 mmol) followed by 1-Bromo-2-methoxymethoxy ethane (22.7 g, 134.0 mmol) in three portions over a 3 h period at room temperature. After 20 h, solid precipitate was removed by filtration and the filtrate was diluted with brine (50 mL) and extracted with ethyl acetate (4×50 mL). The combined extracts were washed with brine, dried (MgSO$_4$), and evaporated to give the desired ester (38.0 g, 97%) as an oily residue which was used in the next reaction without further purification.

Step D: 3,4-Dihydro-3-hydroxymethyl-2-(2-methoxymethoxy)ethyl-2H-thieno [3,2-e]-1,2-thiazine 1,1-dioxide To a solution of the product from Step C (39.0 g, 112 mmol) in ethanol (100 mL) was added solid sodium borohydride (12.8 g, 337 mmol) at room temperature. After 48 h, solvent was evaporated and saturated aqueous solution of ammonium chloride (50 mL) was added followed by 2N HCl (10 mL); this solution was extracted with ethyl acetate (4×50 mL). The combined extracts were washed with brine (100 mL), dried (MgSO$_4$) and evaporated to give an oily residue which was purified by column chromatography (silica, gradient, 60% to 80% ethyl acetate-hexane) to an oil (25.0 g, 73%).

Step E: 3,4-Dihydro-3-hydroxymethyl-2-(2-methoxymethoxy)ethyl-2H-thieno [3,2-e]-1,2-thiazine-6-sulfonamide 1,1-dioxide To a solution of the product from Step D (3.80 g, 12.4 mmol) in THF (70 mL) was added a 2.5M solution of n-butyllithium in hexane (10.80 mL, 27.2 mmol) at −78° C. After 1 h, a stream of sulfur dioxide gas was bubbled over the surface of the solution until it was acidic. The mixture was warmed to room temperature and stirred for 2 h. Evaporation of the solvent gave a residue which was dissolved in water, cooled to 0° C., and sodium acetate trihydrate (8.42 g, 62.0 mmol) was added followed by hydroxylamine-O-sulfonic acid (7.00 g, 62.0 mmol). After 15 min, solid sodium bicarbonate was added until the pH of the solution was neutral; this solution was stirred at room temperature for 15 h and extracted with ethyl acetate (4×50 mL). The combined extracts were washed with brine (100 mL), dried (MgSO$_4$), and evaporated. The residue was dissolved in a minimal amount of methanol and treated with ethyl acetate to give white crystals (3.00 g, 61%); mp 74°–76° C.

Step F: 3,4-Dihydro-2-[(2-hydroxy)ethyl]-3-hydroxymethyl-2H-thieno[2,3-e]-1, 2-thiazine-6-sulfonamide-1,1-dioxide A solution of the product from Step E (2.70 g, 6.9 mmol) in THF (20 mL) and a solution of 2N HCl (50 mL)) were combined and stirred at room temperature. After 48 h, the reaction mixture was diluted with brine (100 mL) and extracted with ethyl acetate (4×50 mL). The combined extracts were washed with brine (20 mL), dried (MgSO$_4$) and evaporated to give an oil (2.50 g, 95%)

Step G: 4,4a,5,6,7,8-Hexahydro-6-[(2-methoxy)ethyl]-pyrazino[1,2-b]thieno[3,2-e]1,2-thiazine-2-sulfonamide 10,10-dioxide To a stirred solution of the product from Step F (2.50 g, 7.3 mmol) in pyridine (10.0 mL) was added p-toluenesulfonyl chloride (4.50 g, 23.0 mmol) at room temperature. After 16 h, brine (50 mL) was added and the mixture extracted with ethyl acetate (4×50 mL). The combined extracts were washed with brine (20 mL), dried (MgSO$_4$), and evaporated. The residue was dissolved in THF (10 mL) and 2-methoxyethylamine (6.40 mL, 73.0 mmol) was added followed by solid barium carbonate (4.30 g, 22.0 mmol); this mixture was refluxed for 36 h. The excess of amine and THF were removed by evaporation, a saturated aqueous solution of ammonium chloride (50 mL) was added and the mixture was extracted with ethyl acetate (4×50 mL). The combined extracts were washed with brine (20 mL), dried (MgSO$_4$), and evaporated to a residue which was purified by column chromatography (silica, gradient, 30% to 60% ethyl acetate-hexane) to give a solid (1.25 g, 45%). Recrystallization from methanol gave white crystals (0.75 g): mp. 224°–225° C.

Analysis. Calculated for $C_{12}H_{19}N_3O_5S_3 \cdot 0.1$ $C_3H_8O$: C, 38.12; H, 5.15; N, 10.84. Found: C, 38.29; H, 5.04; N, 10.88.

EXAMPLE 4

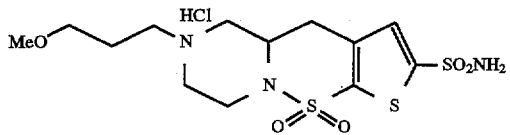

4,4a,5,6,7,8-Hexahydro-6-(3-methoxypropyl)-pyrazino[1,2-b]thieno[3,2-e]-1,2-thiazine-2-sulfonamide 10,10-dioxide hydrochloride By following the procedure described in Example 3, Step G but using instead 3-methoxypropylamine, the title compound was prepared: mp 238°–240° C., recrystallization from 2-propanol.

Analysis. Calculated for $C_{13}H_{22}ClN_3O_5S_3 \cdot 0.1$ $C_3H_8O$: C, 36.47; H, 5.24; N, 9.59. Found: C, 36.47; H, 5.10; N, 9.49.

EXAMPLE 5

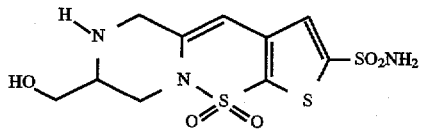

5,6,7,8-Tetrahydro-7-hydroxymethyl-pyrazino[1,2-b]thieno[3,2-e]-1,2-thiazine-2-sulfonamide 10,10-dioxide Step A: (2,2-Dimethyl-1,3-dioxolan4-yl)methyl 4-nitrobenzenesulfonate Pyridine (29.96 g, 0.37 mol) was added to a solution of 4-nitrobenzenesulfonyl chloride (58.7 g, 0.26 mol) in dichloromethane (300 mL) at 0° C. followed by the dropwise addition of 2,2-dimethyl-1,3-dioxolane-4-methanol (50 g, 0.37 mol). After stirring the mixture at temperature for 1 h, the reaction mixture was allowed to warm to room temperature and stirring continued for 4 h. The reaction nitrate was washed with 1N HCl (2×200 mL), dried (MgSO$_4$), and evaporated to a solid which was recrystallized (ethyl acetate/hexane) to give 60 g (50%) of the desired product: mp 92°–94° C.

Step B: Ethyl 2-[(2,2-Dimethyl-1,3-dioxolan-4-yl)methyl]-2H-thieno[3,2-e]-1,2-thiazine-3-carboxylate 1,1-dioxide The product from Step A (46.5 g, 0.292 mol) was added in portions to a solution (room temperature) of (N-[[3-formyl-thien-2-yl]sulfonyl]glycine ethyl ester (27 g, 0.97 mol) in dimethylsulfoxide (200 mL) which contained potassium carbonate (40.45 g, 0.292 mol). This mixture was stirred at 55° C. for 12 h, cooled to 0° C, diluted with water, and extracted with ethyl acetate (3×200 mL). The combined extracts were dried (MgSO$_4$) and evaporated to a crude oil which was purified by column chromatography (silica, 30% ethyl acetate in hexane) to give 18 g (50%) of the desired product as an oil.

Step C: 7-Hydroxymethyl-7,8-dihydro-5H-[1,4]oxazino[4,3-b]thieno[3,2-e]-1,2-thiazine-5-one 10,10-dioxide A solution of the product from Step B (18 g, 21.4 mmol) in a water/trifluoroacetic acid mixture (1:9) was stirred for 12 h. The solid which formed was collected by filtration, washed with hexane, and dried to give 11.9 g (86%) of a colorless solid: mp 210°–212° C.

Step D: 7-[(1-Ethoxyethoxy)methyl]-7,8-dihydro-5H-[1,4]oxazino[4,3-b]thieno[3,2-e]-1,2-thiazine-5-one 10,10-dioxide A suspension of the product from Step C (10 g, 34.84 mmol) in anhydrous THF (200 mL) at 0° C. was combined with ethyl vinyl ether (5.02 g, 69.68 mmol) and p-toluenesulfonic acid (1.32 g, 6.9 mmol); this mixture was stirred until it became homogeneous. The reaction mixture was filtered through silica and the solvent evaporated to give a residue which was purified by column chromatography (silica, ethyl acetate/hexane, 3:7) to give 6.8 g (54%) of an oil.

Step E: 2-[3-(1-ethoxyethoxy)-2-hydroxypropyl]-3-hydroxymethyl-thieno[3,2-e]-1,2-thiazine 1,1-dioxide A 1.0N solution of diisobutylaluminium hydride in hexanes (41.78 mL, 41.78 mmol) was added to a solution of the product from Step E (5.0 g, 13.92 mmol) in THF (100 mL) at 0° C.; this mixture was stirred at 0° C. for 1 h and then at room temperature for 1 h. The excess of reducing agent was destroyed by the careful addition of methanol (5 mL) at 0° C. followed by the addition of a sainted solution of sodium potassium tartate (50 mL) and ethyl acetate (150 mL). The organic layer was separated, dried (MgSO$_4$), and evaporated to a residue which was purified by column chromatography (silica, hexane/acetone, 1:1) to give 4 g (82%) of a solid: mp 95°–97° C.

Step F: 7-[(1-Ethoxyethoxy)methyl]-5,6,7,8-tetrahydropyrazino[1,2-b]thieno[3,2-e]-1,2-thiazine 10,10-dioxide To a solution of the product from Step E (2.5 g, 6.8 mmol) in anhydrous THF (40 mL) at 0° C. was added diisopropylethylamine (2.2 g, 17.2 mmol) followed by methanesulfonic anhydride (2.99 g, 17.2 mmol). This mixture was stirred for 1 h and then allowed to warm to room temperature and stirred for an additional 2 h. The reaction mixture was diluted with ethyl acetate (100 mL) and washed with water (40 mL). The organic layer was dried (MgSO$_4$) and the solvent removed to give the desired dimesylate as an oil. A solution of this oil in THF (10 mL) was added to an excess of liquid ammonia which had been condensed into a glass pressure reactor. The sealed reactor was heated at 65° C. for 12 h, cooled, and the excess of ammonia and solvent were evaporated to give a residue which was purified by column chromatography (silica, hexane/acetone, 1:1) to give 1.5 g (83%) of an oil.

Step G: 7-Methyl-9a,10-dihydro-5H,7H,9H-oxazolo[3',4':4,5]pyrazino[1,2-b]thieno[3,2-e][1,2]thiazine 12,12-dioxide Methane sulfonic anhydride (0.78 g, 4.53 mmol) was added to a solution of the product of Step F (1.3 g, 3.78 mmol) in THF (40 mL) at 0° C. This mixture was stirred for 1 h and then allowed to warm to room temperature and stirred for an additional 2 h. The reaction mixture was washed with a saturated solution of sodium bicarbonate and extracted with ethyl acetate (3×100mL). The combined extracts were dried (MgSO₄) and evaporated to a residue which was purified by column chromatography (silica, acetone/hexane, 1:1) to give 1 g (83%) of an off white amorphous solid.

Step H: 7-Hydroxymethyl-5,6,7,8-tetrahydro-pyrazino[1,2-b]thieno[3,2-e]-1,2-thiazine-2-sulfonamide 10,10-dioxide A solution of the product of Step G (1 g, 3.1 mmol) in THF (20 mL) at −78° C. was treated with 2.5M n-butyllithium (1.86 g, 4.65 mmol), sulfur dioxide, and hydroxylamine-O-sulfonic acid (1.05 g, 9.3 mmol) as described in Example 1, Step F to provide, after column chromatography (silica, methanol/dichloromethane, 1:9), the desired compound (70 mg, 6%) as an off-white solid: mp 170° C. dec.

Analysis. Calculated for $C_{10}H_{13}N_3O_5S_3$: C, 34.18; H, 3.73; N, 11.96. Found: C, 34.42; H, 3.78; N, 11.71.

EXAMPLE 6

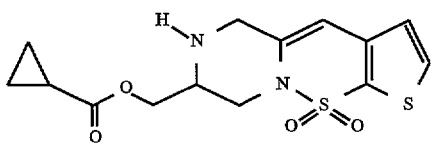

[2-(Aminosulfonyl)-5,6,7,8-tetrahydro-pyrazino[1,2-b]thieno[3,2-e]-1,2-thiazin-7-yl]methyl cyclopropanecarboxylate $S^{10},S^{10}$-dioxide A solution of the product from Example 5 (0.45 g, 1.3 mmol) in trifluoroacetic acid (5 mL) was cooled (0° C.), cyclopropane carbonyl chloride (0.23 mL, 2.55 mmol) was added, and the mixture was stirred for 3 h. The reaction mixture was diluted with ethyl acetate (50 mL) and the mixture neutralized by adding a saturated aqueous solution of sodium bicarbonate (50 mL). The ethyl acetate layer was separated, dried (MgSO₄), and evaporated to a residue which was purified by column chomatography (silica, hexane/acetone, 1:1) to give 0.3 g (56%) of a firm foam: mp 73°–75° C.

Analysis. Calculated for $C_{14}H_{17}N_3O_6S_3$ -0.3 $(CH_3)_2CO$: C, 40.96; H, 4.33; N, 9.61. Found C, 40.94; H, 4.34; N, 9.37.

Using the procedures described in Equations 1 to 4, the Examples 1 to 6, and other well-known procedures, one skilled in the art can prepare the compounds listed in the following Table.

TABLE 1

| R | Z | C4—C4a Bond[1] |
|---|---|---|
| CH₂CH₂OH | H | d or s |
| CH₂CH₂OMe | H | d or s |
| CH₂CH₂CH₂OMe | H | d or s |

TABLE 1-continued

| R | Z | C4—C4a Bond[1] |
|---|---|---|
| CH₂CH₂CH₂OC(=O)C₃H₅ | H | d or s |
| CH₂CH₂C(=O)OiPr | H | d or s |
| CH₂CH₂C(=O)OiPr | CH₃ | d or s |
| H | 7-CH₂OH | d or s |
| H | 7-CH₂OC(=O)C₃H₅ | d or s |
| CH₃ | 7-CO₂OC(=O)C₃H₅ | d or s |
| H | 7-CO₂-iPr | d or s |
| CH₃ | 7-CH₂OH | d or s |
| H | 7-CH₂NHC(=O)CH₃ | d or s |
| CH₂CH₂OH | 7-CH₂OH | d or s |
| CH₂CH₂OAc | 7-CH₂OAc | d or s |
| H | 7-CH₂C₆H₄-(3-MeO) | d or s |
| H | 7-CH₂CH₂OH | d or s |
| H | 7-CH₂C₆H₃-(3,4-OH) | d or s |
| H | 7-CH₂OCH₃ | d or s |

[1]d = double bond; s = single bond.

EXAMPLE 7

Ophthalmic Suspension

| Ingredient | Concentration (wt %) |
|---|---|
| 5,6,7,8-Tetrahydro-6-(2-methoxyethyl)-pyrazino[1,2-b]thieno[3,2-e]-1,2-thiazine-2-sulfonamide 10,10-dioxide (Compound) | 3.0% |
| Hydroxypropylmethylcelluose | 0.5% |
| Dibasic Sodium Phosphate | 0.2% |
| Disodium Edetate | 0.01% |
| Sodium Chloride | 0.8% |
| Purified Water | q.s. |
| Benzalkonium Chloride | 0.01% |
| Polysorbate 80 | 0.1% |
| NaOH/HCl | pH 7.02 |

The compound (0.09 g), benzalkonium chloride (0.03 g), and polysorbate 80 (0.15 g) can be mixed in water (1.23 g) and ball milled for approximately 4 hr. A hydroxypropylmethylcellulose vehicle can be prepared by mixing 2% aqueous hydroxypropylmethylcellulose (40 g), sodium chloride (1.28 g), dibasic sodium phosphate (0.32 g), disodium edetate (0.016 g), sodium chloride (1.28 g) and water (35 g) together and the pH adjusted to 7.4 by the addition of 1N HCl (250 μL). A portion of this vehicle (1.5 mL) can be added to the mixture containing the Compound to furnish the desired suspension.

EXAMPLE 8

Ophthalmic Suspension

| Ingredient | Concentration (wt %) |
|---|---|
| 5,6,7,8-Tetrahydro-7-hydroxymethyl-pyrazino[1,2-b]thieno[3,2-e]-1,2-thiazine-2-sulfonamide 10,10-dioxide (Compound) | 2.0% |
| Hydroxyethylcellulose | 0.5% |

-continued

Ophthalmic Suspension

| Ingredient | Concentration (wt %) |
|---|---|
| Monobasic Sodium Phosphate | 0.13% |
| Dibasic Sodium Phosphate | 0.01% |
| Benzalkonium Chloride | 0.01% |
| Disodium Edetate | 0.01% |
| Purified Water | q.s. |
| NaCl (Osmolality = 282 mOsm) | 0.4% |
| HCl/NaOH | pH 5.0 |

The Compound (0.06 g) and sodium chloride (0.014 g) were mixed together in water (1.44 g) and the pH of the solution was adjusted to 5.02 by the addition of 1N NaOH (10 µL). The hydroxyethylcellulose vehicle was prepared by mixing together monobasic sodium phosphate (0.26 g), dibasic sodium phosphate (0.02 g) and desodium edetate (0.02 g) in water (96.7 g). The benzalkonium chloride (2.0 g) and hydroxyethylcellulose were added to the mixture and the pH eas adjusted to 5.01 by the addition of 1N HCl (100 µL). A portion of this vehicle (1.5 g) was added to the solution containing the compound and the pH was adjusted to 5.03 by the addition of 1N NaOH (10 µL).

EXAMPLE 9

Ophthalmic Gel

| Ingredient | Concentration (wt %) |
|---|---|
| 5,6,7,8-Tetrahydro-6-(2-hydroxyethyl-pyrazino[1,2-b]thieno[3,2-e]-1,2-thiazine-2-sulfonamide 10,10-dioxide (Compound) | 1.0% |
| Mannitol | 3.6% |
| Benzalkonium Chloride | 0.01% |
| Carbopol | 3.0% |
| HCl/NaOH | pH 5.0 |
| Purified Water | q.s. |

The mannitol (0.18 g), benzalkonium chloride (0.05 g), Compound (0.1 g) and carbopol (0.15 g) can all be added to water (4.3 mL) and mixed well. The pH can be adjusted to pH 5.0 and purified water (q.s. to 5 mL) can be added and mixed well to form a gel.

We claim:

1. A compound of the structure:

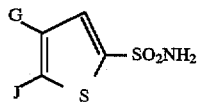

Wherein G, J and the two atoms of the thiophene ring to which they are attached are the group

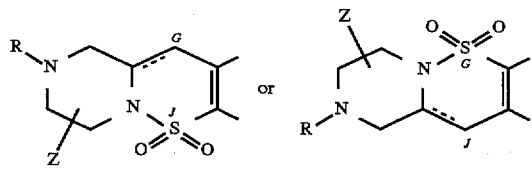

wherein

Z is hydrogen, $C_{1-4}$alkyl, $C_{1-4}$alkyl substituted with one or more of hydroxyl, $C_{1-4}$alkoxy, $C_{2-4}$alkoxy-$C_{1-4}$alkoxy, $OC(=O)R^1$, $N(R^2)C(=O)R^1$, halogen, $NR2R^3$ or $C(=O)R^4$; $C_{1-4}$alkyl substituted with an aromatic group chosen from phenyl or Q, either of which is unsubstituted or substituted with one or more of $C_{1-4}$alkyl, $C_{1-4}$ alkoxy, hydroxy, halogen, $NR^2R^3$, $C(=O)R^4$ or $C_{1-4}$ alkyl which is substituted with hydroxy, $NR^2R^3$, halogen, $CO_2R^1$, or $C_{1-3}$alkoxy;

R is hydrogen, $C_{1-4}$alkyl, $C_{1-4}$alkoxy, $C(=C))R^1$, $C_{1-4}$alkyl substituted by $C_{1-4}$alkoxy, $CO_2$-$C_{1-4}$ alkyl, halo, $NR^2R^3$, $OC(=O)$-$C_{1-4}$alkyl, hydroxyl, or $C(=O)NR^2R^3$;

$R^1$ is $C_{1-6}$alkyl; $C_{1-4}$alkyl substituted with hydroxyl, halogen, $C_{1-4}$alkoxy, or $NR^2R^3$;

$R^2$ and $R^3$ are independently hydrogen;

$C_{1-4}$alkyl;

$C_{1-3}$alkyl-$C_{3-6}$cycloalkyl;

$C_{2-4}$alkyl substituted with hydroxyl, halogen, CN, $C_{1-4}$alkoxy, or $C(=O)R^4$;

hydroxyl;

$C_{1-4}$alkoxy;

$C_{2-4}$alkoxy substituted with hydroxyl, $NR^2R^3$, halogen, or $C_{1-4}$alkoxy;

$C_{3-8}$alkenyl unsubstituted or substituted with hydroxy, or $C_{1-4}$alkoxy; or further $R^2$ and $R^3$ together with the nitrogen atom to which they are attached are incorporated into a saturated heterocyclic ring chosen fore pyrrolidine, oxazolidine, morpholine, thiomorpholine, thiomorpholine 1,1-dioxide, 2-oxa-5-azabicyclo[2.2.1]heptane, 2-oxa-5-azabicyclo[3.2.1]octane, thiazolidine, or thiazolidine 1,1-dioxide, which are unsubstituted or substituted on carbon with hydroxyl, (=O), halogen, $C_{1-4}$alkoxy, $C(=O)R^4$, $C_{1-4}$alkyl, $C_{1-4}$alkyl substituted with hydroxyl, halogen, $C_{1-4}$alkoxy, or $C(=O)R^4$;

$R^4$ is hydroxyl; $C_{1-4}$alkoxy;

$C_{2-4}$alkoxy substituted with hydroxyl, $NR^2R^3$, halogen or $C_{1-4}$alkoxy; $NR^2R^3$;

Q is a heterocycle selected from the group consisting of thiophene, furan, pyrrole, pyrazole, imidazole, triazole, tetrazole, oxazole, isoxazole, isothiazole, thiazole, thiadiazole, pyridine, pyrimidine, pyridazine, and pyrazine.

2. The compound of claim 1 having the structure:

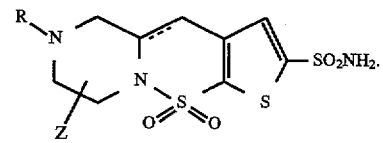

3. The compound of claim 1 having the structure:

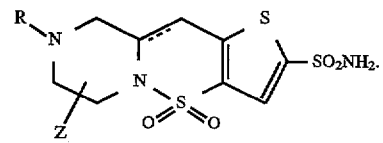

4. The compound of claim 2 wherein Z is at position 7.
5. The compound of claim 4 wherein R is hydrogen.
6. The compound of claim 3 wherein Z is at position 7.
7. A compound selected from the group consisting of:
5,6,7,8-Tetrahydro-6-(2-methoxyethyl)-pyrazino[1,2-b]thieno[3,2-e]-1,2-thiazine-2-sulfonamide 10,10-dioxide 5,6,7,8-Tetrahydro-6-(2-hydroxyethyl)-pyrazino[1,2 -b]thieno[3,2-e]-1,2-thiazine-2-sulfonamide 10,10-dioxide;

4,4a,5,6,7,8-Hexahydro-6-(2-methoxyethyl)-pyrazino[1,2 -b]thieno[3,2-e]-1,2-thiazine-2-sulfonamide 10,10;dioxide;

4,4a,5,6,7,8-Hexahydro-6-(3-methoxypropyl)-pyrazino[1,2-b]thieno[3,2-e]-1,2-thiazine-2-sulfonamide 10,10-dioxide;

5,6,7,8-Tetrahydro-7-hydroxymethyl-pyrazino[1,2-b]thieno[3,2-e]-1,2-thiazine-2-sulfonamide 10,10-dioxide; and

[2-(Aminosulfonyl)-5,6,7,8-tetrahydro-pyrazino[1,2-b]thieno[3,2-e]-1,2-thiazin-7-yl]methyl cyclopropanecarboxylate $S^{10}$, $S^{10}$-dioxide.

8. A composition for controlling intraocular pressure comprising a pharmaceutically effective amount of a compound of the structure:

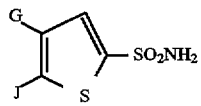

Wherein G, J and the two atoms of the thiophene ring to which they are attached are the group

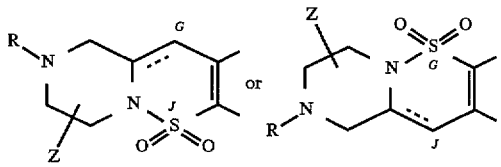

wherein

Z is hydrogen, $C_{1-4}$alkyl, $C_{1-4}$alkyl substituted with one or more of hydroxyl, $C_{1-4}$alkoxy, $C_{2-4}$alkoxy-$C_{1-4}$alkoxy, $OC(=O)R^1$, $N(R^2)C(=O)R^1$, halogen, $NR^2R^3$ or $C(=O)R^4$; $C_{1-4}$alkyl substituted with an aromatic group chosen from phenyl or Q, either of which is unsubstituted or substituted with one or more of $C_{1-4}$alkyl, $C_{1-4}$alkoxy, hydroxy, halogen, $NR^2R^3$, $C(=O)R^4$ or $C_{1-4}$alkyl which is substituted with hydroxy, $NR^2R^3$, halogen, $CO^2R^1$, or $C_{1-3}$alkoxy;

R is hydrogen, $C_{1-4}$alkyl, $C_{1-4}$alkoxy, $C(=O)R^1$, $C_{1-4}$alkyl substituted by $C_{1-4}$alkoxy, $CO^2$-$C_{1-4}$ alkyl, halo, $NR^2R^3$, $OC(=O)$-$C_{1-4}$alkyl, hydroxyl, or $C(=O)$ $NR^2R^3$;

$R^1$ is $C_{1-6}$alkyl; $C_{1-4}$alkyl substituted with hydroxyl, halogen, $C_{1-4}$alkoxy, or $NR^2R^3$;

$R^2$ and $R^3$ are independently hydrogen;

$C_{1-4}$alkyl;

$C_{1-3}$alkyl-$C_{3-6}$cycloalkyl;

$C_{2-4}$alkyl substituted with hydroxyl, halogen, CN, $C_{1-4}$alkoxy, or $C(=O)R^4$;

hydroxyl;

$C_{1-4}$alkoxy;

$C_{2-4}$alkoxy substituted with hydroxyl, $NR^2R^3$, halogen, or $C_{1-4}$alkoxy;

$C_{3-8}$alkenyl unsubstituted or substituted with hydroxy, or $C_{1-4}$alkoxy; or further $R^2$ and $R^3$ together with the nitrogen atom to which they are attached are incorporated into a saturated heterocyclic ring chosen from pyrrolidine, oxazolidine, morpholine, thiomorpholine, thiomorpholine 1,1-dioxide, 2-oxa-5-azabicyclo[2.2.1]

heptane, 2-oxa-5-azabicyclo[3.2.1]octane, thiazolidine, or thiazolidine 1,1-dioxide, which are unsubstituted or substituted on carbon with hydroxyl, (=O), halogen, $C_{1-4}$alkoxy, $C(=O)R^4$, $C_{1-4}$alkyl, $C_{1-4}$alkyl substituted with hydroxyl, halogen, $C_{1-4}$alkoxy, or $C(=O)R^4$;

$R^4$ is hydroxyl; $C_{1-4}$alkoxy;

$C_{2-4}$alkoxy substituted with hydroxyl, $NR^2R^3$, halogen or $C_{1-4}$alkoxy; $NR^2R^3$;

Q is a heterocycle selected from the group consisting of thiophene, furan, pyrrole, pyrazole, imidazole, triazole, tetrazole, oxazole, isoxazole, isothiazole, thiazole, thiadiazole, pyridine, pyrimidine, pyridazine, and pyrazine in a pharmaceutically acceptable carrier.

9. The composition of claim 8 wherein the compound has the structure:

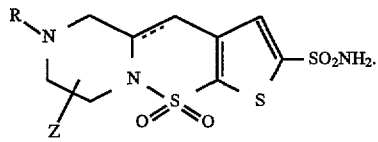

10. The composition of claim 8 wherein the compound has the structure:

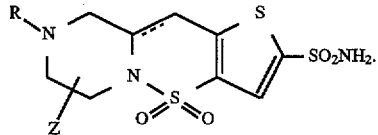

11. The composition of claim 9 wherein Z is at position 7.

12. The composition of claim 11 wherein R is hydrogen.

13. The composition of claim 10 wherein Z is at position 7.

14. A composition for controlling intraocular pressure comprising a pharmaceutically effective amount of a compound selected from the group consisting of:

5,6,7,8-Tetrahydro-6-(2-methoxyethyl)-pyrazino[1,2-b]thieno[3,2-e]-1,2-thiazine-2-sulfonamide 10,10-dioxide 5,6,7, 8-Tetrahydro-6-(2-hydroxyethyl)-pyrazino[1,2-b]thieno[3,2-e]-1,2-thiazine-2-sulfonamide 10,10-dioxide;

4,4a,5,6,7,8-Hexahydro-6-(2-methoxyethyl)-pyrazino[1,2 -b]thieno[3,2-e]-1,2-thiazine-2-sulfonamide 10,10-dioxide;

4,4a,5,6,7,8-Hexahydro-6-(3-methoxypropyl)-pyrazino[1,2-b]thieno[3,2-e]-1,2-thiazine-2-sulfonamide 10,10-dioxide;

5,6,7,8-Tetrahydro-7-hydroxymethyl-pyrazino[1,2-b]thieno[3,2-e]-1,2-thiazine-2-sulfonamide 10,10-dioxide; and

[2-(Aminosulfonyl)-5,6,7,8-tetrahydro-pyrazino[1,2-b]thieno[3,2-e]-1,2-thiazin-7-yl]methyl cyclopropanecarboxylate $S^{10}$, $S^{10}$-dioxide in pharmaceutically acceptable carrier.

15. A method for controlling intraocular pressure in a mammal suffering therefrom which comprises, administering a composition comprising a pharmaceutically effective amount of a compound having the structure:

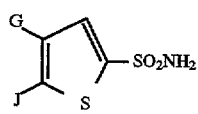

Wherein G, J and the two atoms of the thiophene ring to which they are attached are the group

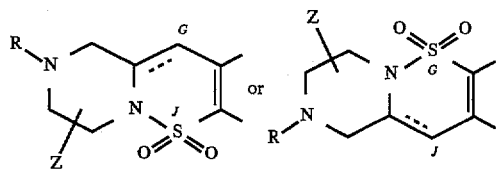

wherein

Z is hydrogen, $C_{1-4}$alkyl, $C_{1-4}$alkyl substituted with one or more of hydroxyl, $C_{1-4}$alkoxy, $C_{2-4}$alkoxy-$C_{1-4}$alkoxy, $OC(=O)R^1$, $N(R^2)C(=O)R^1$, halogen, $NR^2R^3$ or $C(=C))R^4$; $C_{1-4}$alkyl substituted with an aromatic group chosen from phenyl or Q, either of which is unsubstituted or substituted with one or more of $C_{1-4}$alkyl, $C_{1-4}$ alkoxy, hydroxy, halogen, $NR^2R^3$, $C(=O)R^4$ or $C_{1-4}$alkyl which is substituted with hydroxy, $NR^2R^3$, halogen, $CO_2R^1$, or $C_{1-3}$alkoxy;

R is hydrogen, $C_{1-4}$alkyl, $C_{1-4}$alkoxy, $C(=O)R^1$, $C_{1-4}$alkyl substituted by $C_{1-4}$alkoxy, $CO_2$-$C_{1-4}$ alkyl, halo, $NR^2R^3$, $OC(=O)$-$C_{1-4}$alkyl, hydroxyl, or $C(=O)$ $NR^2R^3$;

$R^1$ is $C_{1-6}$alkyl; $C_{1-6}$alkyl substituted with hydroxyl, halogen, $C_{1-4}$alkoxy, or $NR^2R^3$;

$R^2$ and $R^3$ are independently hydrogen;

$C_{1-4}$alkyl;

$C_{1-3}$alkyl-$C_{3-6}$cycloalkyl;

$C_{2-4}$alkyl substituted with hydroxyl, halogen, CN, $C_{1-4}$alkoxy, or $C(=C))R^4$;

hydroxyl;

$C_{1-4}$alkoxy;

$C_{2-4}$alkoxy substituted with hydroxyl, $NR^2R^3$, halogen, or $C_{1-4}$alkoxy;

$C_{3-8}$alkenyl unsubstituted or substituted with hydroxy, or $C_{1-4}$alkoxy; or further $R^2$ and $R^3$ together with the nitrogen atom to which they are attached are incorporated into a saturated heterocyclic ring chosen from pyrrolidine, oxazolidine, morpholine, thiomorpholine, thiomorpholine 1,1-dioxide, 2-oxa-5-azabicyclo[2.2.1] heptane, 2-oxa-5-azabicyclo[3.2.1]octane, thiazolidine, or thiazolidine 1,1-dioxide, which are unsubstituted or substituted on carbon with hydroxyl, (=O), halogen, $C_{1-4}$alkoxy, $C(=C))R^4$, $C_{1-4}$alkyl, $C_{1-4}$alkyl substituted with hydroxyl, halogen, $C_{1-4}$alkoxy, or $C(=O)$ $R^4$;

$R^4$ is hydroxyl; $C_{1-4}$alkoxy;

$C_{2-4}$alkoxy substituted with hydroxyl, $NR^2R^3$, halogen or $C_{1-4}$alkoxy; $NR^2R^3$;

Q is a heterocycle selected from the group consisting of thiophene, furan, pyrrole, pyrazole, imidazole, triazole, tetrazole, oxazole, isoxazole, isothiazole, thiazole, thiadiazole, pyridine, pyrimidine, pyridazine, and pyrazine.

16. The method of claim 15 wherein the compound has the structure:

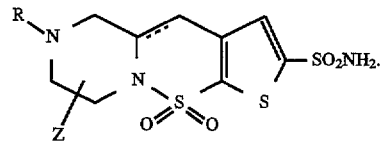

17. The method of claim 15 wherein the compound has the structure:

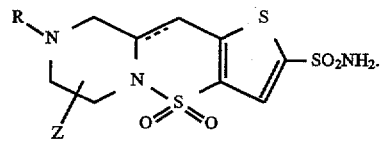

18. The method of claim 16 wherein Z is at position 7.
19. The method of claim 18 wherein R is hydrogen.
20. The method of claim 17 wherein Z is at position 7.
21. A method for controlling intraocular pressure which comprises, administering a composition comprising a pharmaceutically effective amount of a compound selected from the group consisting of:

5,6,7,8-Tetrahydro-6-(2-methoxyethyl)-pyrazino[1,2-b]thieno[3,2-e]-1,2-thiazine-2-sulfonamide 10,10-dioxide 5,6,7,8-Tetrahydro-6-(2-hydroxyethyl)-pyrazino[1,2-b]thieno[3,2-e]-1,2-thiazine-2-sulfonamide 10,10-dioxide;

4,4a,5,6,7,8-Hexahydro-6-(2-methoxyethyl)-pyrazino[1,2-b]thieno[3,2-e]-1,2-thiazine-2-sulfonamide 10,10-dioxide;

4,4a,5,6,7,8-Hexahydro-6-(3-methoxypropyl)-pyrazino[1,2-b]thieno[3,2-e]-1,2-thiazine-2-sulfonamide 10,10-dioxide;

5,6,7,8- Tetrahydro-7-hydroxymethyl-pyrazino[1,2-b]thieno[3,2-e]-1,2-thiazine-2-sulfonamide 10,10-dioxide; and

[2-(Aminosulfonyl)-5,6,7,8-tetrahydro-pyrazino[1,2-b]thieno[3,2-e]-1,2-thiazin-7-yl]methyl cyclopropanecarboxylate $S^{10}$, $S^{10}$-dioxide.

* * * * *